(12) United States Patent
Gleeson et al.

(10) Patent No.: US 9,072,815 B2
(45) Date of Patent: Jul. 7, 2015

(54) LAYERED COLLAGEN AND HA SCAFFOLD SUITABLE FOR OSTEOCHONDRAL REPAIR

(71) Applicant: ROYAL COLLEGE OF SURGEONS IN IRELAND, Dublin (IE)

(72) Inventors: John P. Gleeson, Dublin (IE); Tanya J. Levingstone, Wicklow (IE); Fergal J. O'Brien, Dublin (IE)

(73) Assignee: ROYAL COLLEGE OF SURGEONS IN IRELAND, Dublin (IE)

( * ) Notice: Subject to any disclaimer, the term of this patent is extended or adjusted under 35 U.S.C. 154(b) by 0 days.

(21) Appl. No.: 14/084,164

(22) Filed: Nov. 19, 2013

(65) Prior Publication Data
US 2014/0105954 A1 Apr. 17, 2014

Related U.S. Application Data

(62) Division of application No. 13/145,970, filed as application No. PCT/IE2010/000005 on Jan. 25, 2010, now Pat. No. 8,613,943.

(60) Provisional application No. 61/147,006, filed on Jan. 23, 2009.

(30) Foreign Application Priority Data

Jan. 23, 2009 (EP) .................................... 09151226

(51) Int. Cl.
*A61L 27/26* (2006.01)
*A61L 15/28* (2006.01)
(Continued)

(52) U.S. Cl.
CPC ................. *A61L 27/26* (2013.01); *A61L 15/28* (2013.01); *A61L 15/325* (2013.01); *A61L 27/24* (2013.01); *A61L 27/425* (2013.01); *A61L 27/46* (2013.01); *A61L 27/56* (2013.01); *A61L 27/20* (2013.01)

(58) Field of Classification Search
CPC ............................... A61L 15/28; A61L 15/325
See application file for complete search history.

(56) References Cited

U.S. PATENT DOCUMENTS

| 5,899,939 A | 5/1999 | Boyce et al. |
| 6,214,049 B1 | 4/2001 | Gayer et al. |

(Continued)

FOREIGN PATENT DOCUMENTS

| EP | 1961433 A1 | 8/2008 |
| WO | 96/24310 | 5/1996 |

(Continued)

OTHER PUBLICATIONS

Tampieri et al, "Design of Graded Biomimetic Osteochondral Composite Scaffolds", Biomaterials, Elsevier Science Publishers, vol. 29, No. 26, Sep. 1, 2008.*

(Continued)

*Primary Examiner* — Carlos Azpuru
(74) *Attorney, Agent, or Firm* — Nixon Peabody LLP

(57) ABSTRACT

The invention relates to a method for producing a multi-layer collagen scaffold. The method generally comprises the steps of: preparing a first suspension of collagen and freezing or lyophilising the suspension to provide a first layer; optionally preparing a further suspension of collagen and adding the further suspension onto the layer formed in the previous step to form a further layer, and freezing or lyophilising the layers, wherein when the layer formed in the previous step is formed by lyophilisation the lyophilised layer is re-hydrated prior to addition of the next layer; optionally, repeating the aforementioned step to form one or more further layers; and preparing a final suspension of collagen and pouring the final suspension onto the uppermost layer to form a final layer, and freeze-drying the layers to form the multi-layer collagen composite scaffold.

15 Claims, 7 Drawing Sheets

(51) Int. Cl.

| | |
|---|---|
| A61L 15/32 | (2006.01) |
| A61L 27/24 | (2006.01) |
| A61L 27/42 | (2006.01) |
| A61L 27/46 | (2006.01) |
| A61L 27/56 | (2006.01) |
| A61L 27/20 | (2006.01) |

(56) References Cited

U.S. PATENT DOCUMENTS

| | | |
|---|---|---|
| 6,599,516 B1 | 7/2003 | Knaack |
| 6,626,950 B2 | 9/2003 | Brown et al. |
| 6,649,162 B1 | 11/2003 | Biering et al. |
| 7,175,852 B2 | 2/2007 | Simmoteit et al. |
| 7,229,545 B2 | 6/2007 | Sewing et al. |
| 7,375,077 B2 | 5/2008 | Mao |
| 7,537,617 B2 | 5/2009 | Bindsell et al. |
| 7,709,018 B2 | 5/2010 | Pastorello et al. |
| 7,763,272 B2 | 7/2010 | Offermann et al. |
| 8,039,090 B2 | 10/2011 | Kawamura et al. |
| 8,182,532 B2 | 5/2012 | Anderson et al. |
| 8,183,041 B2 | 5/2012 | Liao et al. |
| 2002/0042657 A1 | 4/2002 | Pugh et al. |
| 2003/0003127 A1 | 1/2003 | Brown et al. |
| 2005/0043813 A1 | 2/2005 | Kusanagi et al. |
| 2005/0100578 A1 | 5/2005 | Schmid et al. |
| 2006/0083729 A1 | 4/2006 | Kusanagi et al. |
| 2006/0195179 A1 | 8/2006 | Sun et al. |
| 2007/0026069 A1 | 2/2007 | Shastri et al. |
| 2007/0041952 A1 | 2/2007 | Guilak et al. |
| 2008/0020049 A1 | 1/2008 | Darling et al. |
| 2010/0145468 A1 | 6/2010 | Shoji |
| 2010/0166828 A1 | 7/2010 | Shoji |
| 2011/0182962 A1 | 7/2011 | McKay |

FOREIGN PATENT DOCUMENTS

| | | |
|---|---|---|
| WO | 99/19005 | 4/1999 |
| WO | 02/15881 A2 | 2/2002 |
| WO | 2004/111643 A2 | 12/2004 |
| WO | 2005/051447 A1 | 6/2005 |
| WO | 2006/095154 A2 | 9/2006 |
| WO | 2006092718 A2 | 9/2006 |
| WO | 2008/012828 A2 | 1/2008 |
| WO | 2008/017858 A2 | 2/2008 |
| WO | 2008/096334 | 8/2008 |
| WO | 2008/157608 A1 | 12/2008 |
| WO | 2009/097534 A1 | 8/2009 |
| WO | 2010/117389 A1 | 10/2010 |
| WO | 2011/064724 A1 | 6/2011 |
| WO | 2011/107807 A2 | 9/2011 |
| WO | 2011/156319 A2 | 12/2011 |
| WO | 2012/063201 A1 | 5/2012 |

OTHER PUBLICATIONS

Lu et al., "Construction of tissue engineering cartilage with collagen/hydroxyapatite composite scaffolds loaded chondrocytes in vitro" Chinese Journal of Clinical Rehabilitation, 10(25):177-180, Jul. 10, 2006.

Tampieri et al., "Design of graded biomimetic osteochondral composite scaffolds" Biomaterials, 29(26):3539-3546, Sep. 1, 2008.

Wu et al., "Fabrication of layered scaffold for cartilage tissue engineering" Chinese Journal of Biomedical Engineering 26(4):612-617, Aug. 1, 2007.

PCT Written Opinion of the International Searching Authority for International Application No. PCT/IE2010/000005, mailed May 3, 2010, 10 pgs.

Engler et al., "Matrix elasticity directs stem cell lineage specification" Cell, 126:677-689 (2006).

Harada et al., "Differential effects of different forms of hydroxyapatite and hydroxyapatite/tricalcium phosphate particulates on human monocyte/macrophages in vitro" Journal of Biomedical Materials Research, 31:19-26 (1996).

Hornez et al., "Biological and physico-chemical assessment of hydroxyapatite (HA) with different porosity" Biomolecular Engineering, 24:505-509 (2007).

Kanungo et al., "Characterization of mineralized collagen-glycosaminoglycan scaffolds for bone regeneration" Acta Biomaterialia, 4:490-503 (2008).

Kikuchi et al., "Biomimetic synthesis of bone-like nanocomposites using the self-organization mechanism of hydroxyapatite and collagen" Composites Science and Technology, 64:819-825 (2004).

Nadra et al., "Effect of particle size on hydroxyapatite crystal-induced tumor necrosis factor alpha secretion by macrophages" Atherosclerosis, 196:198-105 (2008).

Rouahi et al., "Quantitative kinetic analysis of gene expression during human osteoblastic adhesion on orthopaedic materials" Biomaterials, 2829-2844 (2006).

Taqvi et al., "Influence of scaffold physical properties and stromal cell coculture on hematopoietic differentiation of mouse embryonic stem cells" Biomaterials 27:6024-6031 (2006).

Tsuruga et al., "Pore size of porous hydroxyapatite as the cell-substratum controls BMP-induced osteogenesis" J. Biochem., 121:317-324 (1997).

O'Brien et al., "Influence of freezing rate on pore structure in freeze-dried collagen-GAG scaffolds" Biomaterials, 25:1077-1086 (2004).

Beris et al. "Advances in articular cartilage repair" The International Journal of the Care of the Injured 36S, S14-S23 (2005).

Sherwood et al. "A three-dimensional osteochondral composite scaffold for articular cartilage repair" Biomaterials 23:4739-4751 (2002).

Lee et al. "Matrices and scaffolds for delivery of bioactive molecules in bone and cartilage tissue engineering" Advanced Drug Delivery Reviews 59:339-359 (2007).

O'Brien et al. "The effect of pore size on cell adhesion in collagen-gag scaffolds" Biomaterials 26:433-441 (2005).

Murphy et al. "The effect of mean pore size on cell attachment, proliferation and migration in collagen-glycosaminoglycan scaffolds for bone tissue engineering" Biomaterials 31(3):461-466 (2010).

* cited by examiner

Figure 4
Figure 5
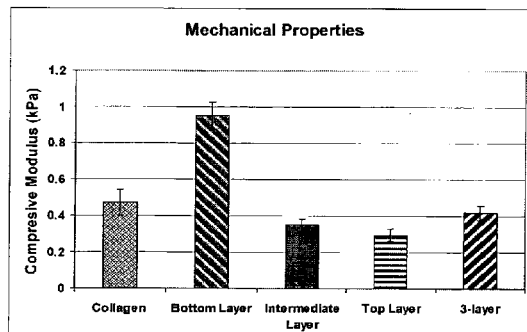
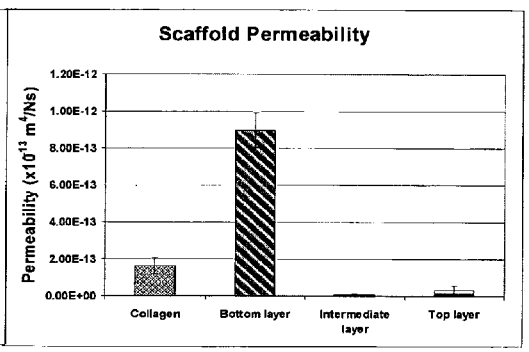
Figure 6
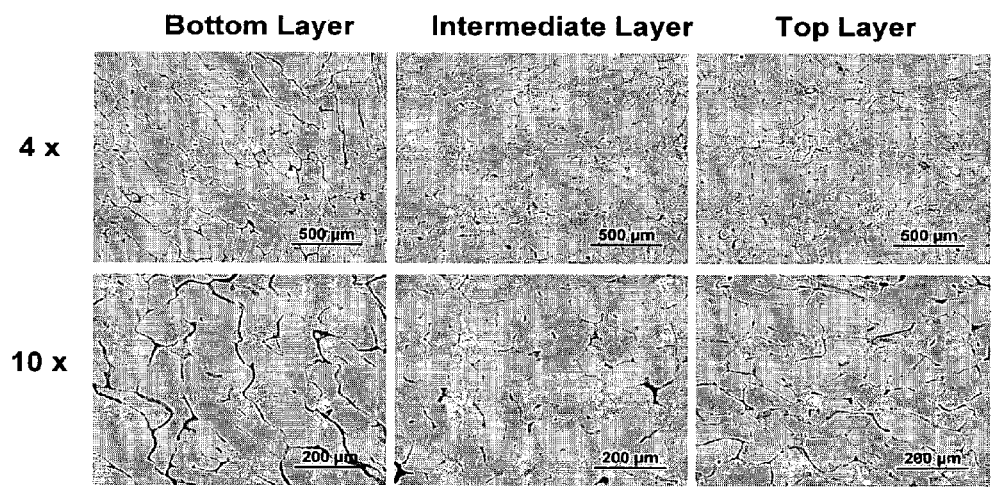

Figure 10
Figure 11
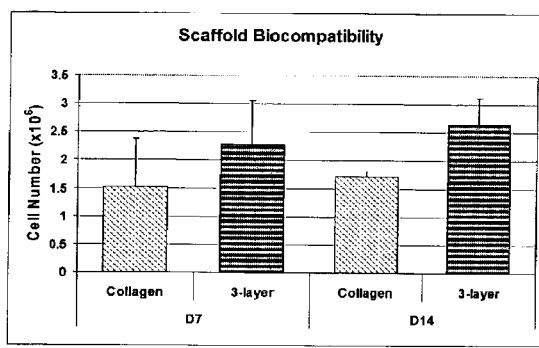
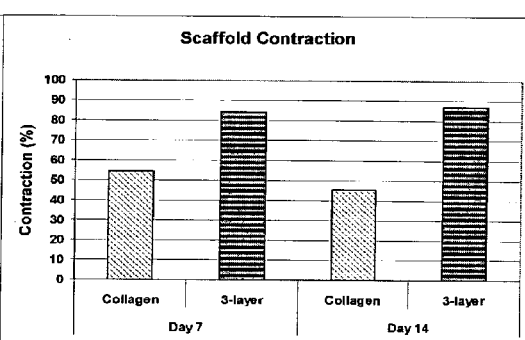
Figure 12
Day 14 – 20x
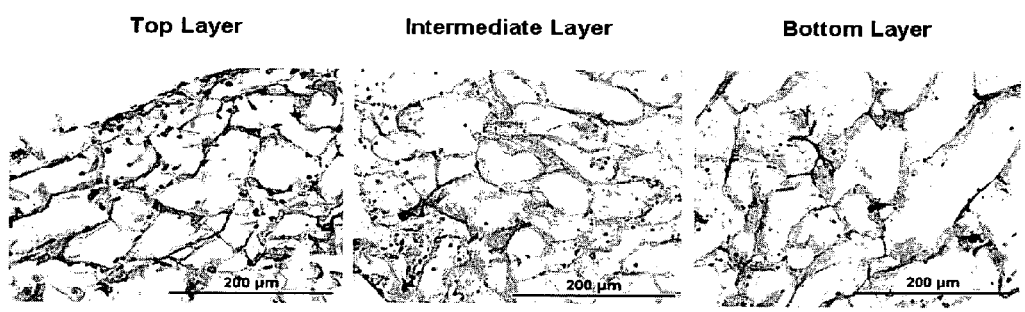

LAYERED COLLAGEN AND HA SCAFFOLD SUITABLE FOR OSTEOCHONDRAL REPAIR

CROSS-REFERENCE TO RELATED APPLICATIONS

This application is a divisional application of U.S. patent application Ser. No. 13/145,970 filed on Oct. 6, 2011, which is a national phase application under 35 U.S.C. §371 of International Application No. PCT/IE2010/000005, filed on Jan. 25, 2010, which claims priority to and the benefit of U.S. Provisional Application No. 61/147,006, filed Jan. 23, 2009 and European Patent Application No. 09151226.9, filed Jan. 23, 2009, the contents of each of which are incorporated herein by reference in their entireties.

INTRODUCTION

The invention relates to a method for producing a multi-layer collagen scaffold suitable for osteochondral defect repair. The invention also relates to a multi-layer collagen-composite scaffold, and uses thereof in osteochondral defect repair.

Articular cartilage is a highly specialised tissue found covering the surfaces of the bony ends of all synovial joints in the human body. Its function is to lubricate joint movement and absorb small shock impacts within a joint. Articular cartilage is composed of 70-80% water, 9% aggrecan (the main water binding molecule within the collagen matrix), 15% collagens (80% type II, 15% type IX and XI and 5% type III, VI, XII, XIV) and 3% cells (Aigner T, Stove J.; 2003).

The structure and composition of articular cartilage is highly ordered into distinct but seamlessly integrated layers which vary in composition and structure according to the distance from the surface. It is typically divided into four zones, superficial, middle (transitional), deep (radial) and calcified cartilage. The superficial zone is a thin dense layer which forms the gliding surface of the joint and provides support and protection. It is composed of thin collagen fibrils aligned parallel to the joint surface, with elongated inactive chondrocytes also aligned with the surface. The middle zone is thicker than the superficial zone and contains spherical cells and larger collagen fibrils that are orientated in a more random fashion. In the deep zone the cells are spherical and are arranged in columnar orientation. Collagen fibrils in this zone are arranged perpendicular to the surface and insert into the calcified cartilage zone providing a transition and mechanical fixation between cartilage and bone (Newman A P.; 1998). Beneath the calcified cartilage zone lies the subchondral bone. Cartilage has a poor ability to regenerate itself due to the sparse distribution and low mitotic activity (differentiation) of the articular chondrocytes and the avascular nature of the tissue.

Superficial damage to the articular cartilage almost inevitably leads to the development of osteoarthritis (OA) within a joint. Cartilage damage and osteoarthritis affect at least 40 million Americans alone per annum, with an associated cost of approximately $105 billion. OA is estimated to be the fourth leading cause of disability by 2020; affecting 9.6% of men and 18% of women aged over 60 years in Europe (Market devices/drivers; Mintel April 2007). Currently used surgical repair techniques fall into three categories: 1) osteochondral grafting, 2) bone marrow stimulation techniques and 3) Autologous Chondrocyte Implantation (ACI). Osteochondral grafting or mosaicplasty involves the removal of cylindrical osteochondral pieces from non-weight bearing areas of the articular cartilage and subsequent transfer of these cylindrical plugs into debrided full thickness defects. Osteochondral grafts can be autologous or allologous, depending on the defect size (allografts being used for larger defects). The major disadvantage of autografts is the risk of donor site morbidity. The disadvantages of allografts include the risk of disease transmission and tissue rejection.

Bone marrow stimulation techniques include abrasive chondroplasty, Pridie drilling and the microfracture technique. These techniques are all aimed at surgically creating access to the bone marrow, allowing blood flow into the defect site which in turn induces spontaneous repair (Beris A E; 2005). This forms a blood clot which traps proteins, lipids, red and white blood cells, platelets, growth factors and blood borne cells (Hunziker E B, 2001). Spontaneous repair occurs in the area, usually consisting of the production of fibrocartilaginous tissue (Beris A E; 2005). In the Pridie drilling technique, 2.0-2.5 mm diameter holes are drilled into the subchondral bone marrow space in areas beneath the lesion. The microfracture technique is a modification of Pridie drilling, the only difference being that the holes drilled are considerably smaller (approximately 0.5 to 1.0 mm in diameter). The success with these surgical techniques has been limited as the fibrocartilage repair tissue which forms has poor mechanical properties, does not perform as well as hyaline cartilage and degenerates over time.

The Autologous Chondrocyte Implantation (ACI) technique involves implantation of chondrocytes into the defect site. It is a two stage process; the first step involves harvesting healthy articular cartilage segments in order to obtain chondrocytes. These chondrocytes are cultured in vitro until sufficient numbers have been produced for implantation into the defect. The second step involves clearing the lesion to reveal healthy cartilage and subchondral bone. A piece of periosteum is then sutured across the lesion and cultured chondrocytes are inserted into the defect, beneath this periosteal layer. The cells then attach to the defect walls and produce extracellular matrix. The disadvantages of this technique include poor retention of the implanted cells within the defect site and phenotypic transformation and dedifferentiation of chondrocytes during expansion in vitro. The defect site is also incapable of load bearing and requires protection for the duration of the recovery period which may be several months.

More recently, membranes and scaffolds have been developed for the repair of cartilage tissue, both alone and in combination with growth factors and cells. One example of the use of scaffolds in cartilage repair is Matrix-induced Autologous Chondrocyte Implantation (MACI, Genzyme, The Netherlands) which involves the seeding of cells in a membrane prior to implantation resulting in better retention of cells in the defect site. Other commercial examples of scaffolds used for cartilage repair include Chondro-Gide, (Geistlich), CaReS®-Cartilage Repair System (Arthro Kinetics), Neocyte (Advanced Tissue Sciences (ATS), Atelocollagen (Koken), Menaflex (ReGen Biologics), and Chondromimetic (Orthomimetics). A number of research groups are currently developing alternative cartilage repair scaffolds using various materials; including polyglycolic acid (PGA), polylactic acid (PLA), collagen, gelatin and fibrin, and various scaffold production techniques; including freeze-drying, solid free-form fabrication, compaction and gelation.

The need for layered scaffolds for osteochondral defect repair has also been identified and as a result, layered scaffold constructs are beginning to emerge. Layered methods that have been used include suturing (WO 96/024310) or gluing (US 2006/0083729 A1) the layers together.

Disadvantages with these techniques include the introduction of an additional material into the defect site, (i.e. the suture material or adhesive) and also the possibility of voids being present at the interface between the two materials, leading to lower interfacial adhesion strength and reduced cellular infiltration.

Solid-free form fabrication techniques have also been used to produce layered scaffolds (Sherwood J K, et al.; 2002). Other layered scaffolds have been produced using a combination of a base ceramic scaffold produced though compaction and sintering and polymer scaffold top layers produced through freeze-drying or gelation of the top scaffold layer (U.S. Pat. No. 0,113,951).

Tampieri et al. (Design of graded biomimetic osteochondral composite scaffolds, Biomaterials, vol 29, no 26, September 2008) describes a 3-layered scaffold, with each layer containing varying amounts of collagen, hyaluronic acid, hydroxyapatite and magnesium-hydroxyapatite. The individual layers were producing by combining the various components to form gels, which were then crosslinked. The layered structure was produced using a knitting procedure. The multi-layer construct was then freeze-dried using a freezing temperature of $-25°$ C. The method used in Tampieri to produce the cartilaginous upper layer involves adding NaOH to a 1 wt % type 1 collagen suspension to form a gel. Hyaluronic acid was added to the gel. The intermediate bony layer (tidemark) and lower bony layer were produced by adding different quantities of $H_3PO_4$ and $Ca(OH)_2$ to allow the formation of hydroxyapatite through a direct nucleation process. The gels were cross-linked using the cross-linking agent 1,4 butanediol diglycidyl ether (BDDGE). The layers were then piled up and a knitting procedure was used to avoid delamination of the layers at the interface. The use of a knitting procedure is disadvantageous as it requires the use of addition non-collagenous materials, such as PGA or PLA fibres, which have an effect on the biocompatibility of the scaffold. Using a knitting procedure also damages the pore structure of the scaffold and results in seams or areas of heterogeneous lamination at the interface between layers. As a result cellular infiltration through the scaffold is restricted. Additionally, freeze-drying of the entire scaffold is carried out in one step and as a result the structure of the individual layers cannot be separately controlled.

STATEMENTS OF INVENTION

The invention relates to a multilayer scaffold suitable for use in tissue-engineering applications, for example, osteochondral defect repair, tendon and ligament repair, vascular repair, tracheal defect repair, and skin repair. The multilayer scaffold of the invention in its simplest form comprises two layers, but may comprise three, four or more layers. The scaffold is made using a process which employs an iterative freezing technique, whereby each layer is subjected to an individual freezing step. Each step may be simply freezing, or freezing followed by sublimation under vacuum (hereafter "lyophilisation" or "freeze-drying"). In each case, the freezing step ideally employs a controlled constant cooling rate freezing method The purpose of this iterative freezing technique is to allow fabrication of each layer using conditions which are independent of each other which, in turn, allows each layer to have different characteristics (for example, different pore morphology and pore architecture). The iterative freezing technique of the process of the invention also provides a multi-layer scaffold in which the distinct layers are seamlessly integrated—that is to say, the pore structure is continuous across the different layers. When freezing alone is employed to produce a layer in the scaffold, the next layer may simply be poured onto the formed layer in the form of a slurry. However, when lyophilisation is employed to form a layer, the lyophilised layer is typically re-hydrated prior to the next layer being poured. The final step typically involves lyophilisation of the multi-layer structure to provide the formed scaffold. As an example, a process of the invention for forming a two-layer scaffold involves forming a first layer by freezing or lyophilisation, pouring a second slurry onto the first layer, and lyophilising the two layers to produce a two-layer scaffold, wherein when the first layer is formed by lyophilisation (as opposed to freezing alone) and is re-hydrated prior to the second layer being formed. Fabrication of such a 2-layer construct is described in embodiment 1. This process can then be repeated to produce further layers. The fabrication of a 3-layer scaffold in which the compositions of the constituent layers of the structure are designed to closely replicate the morphology and composition of anatomical osteochondral tissue is described in embodiment 2.

According to the invention, there is provided a method for producing a multi-layer collagen scaffold comprising the steps of:
  A. preparing a first suspension of collagen and freezing or lyophilising the suspension to provide a first layer;
  B. optionally preparing a further suspension of collagen and pouring the further suspension onto the layer formed in the previous step to form a further layer, and freezing or lyophilising the layers, wherein when the layer formed in the previous step is formed by lyophilisation the lyophilised layer is re-hydrated prior;
  C. optionally, repeating step B to form one or more further layers; and
  D. preparing a final suspension of collagen and pouring the final homogenous suspension onto the uppermost layer to form a final layer, and freeze-drying the layers to form the multi-layer collagen composite scaffold.

The process of the invention provides a multi-layer collagen scaffold in which each layer is formed in a separate freezing or lyophilisation step. As such, the freezing or lyophilisation conditions of each step may be independently varied which allows the pore structure of each layer of the layered scaffold to be individually optimised. This is of vital importance as chondrocytes and osteoblasts require vastly different conditions for optimal in vivo behaviour (Engler et al., 2006). This is distinct from the process described in Tampieri et al. in which each layer is formed independently as a gel, the different layers are physically sutured together, and all layers are lyophilised in a single step using the same lyophilisation conditions. Thus, while the method described by Tampieri et al. allows for the production of a scaffold having layers which are compositionally distinct, the fact that all layers are lyophilised together means that the pore architecture in each layer cannot be independently controlled or varied. Additionally, the step of suturing layers together followed by a single lyophilisation step results in large voids being formed at the interface between layers, and a discontinuous pore architecture across the scaffold (see FIGS. 1 and 8 in Tampieri et al.). This is in contrast to the scaffolds made using the process of the invention in which the pore architecture across the layers is continuous and seamless, and uninterrupted by seams or large voids (See FIG. 9 below). In the present invention the scaffold is produced using an iterative layering technique, where the layers are either frozen or freeze-dried and rehydrated prior to addition of the following layer.

Ideally, one more or all of the suspensions of collagen are homogenous suspensions.

Suitably, each layer is typically compositionally distinct.

Thus, the invention relates to a process for producing a multi-layer scaffold in which each layer typically has a porous structure, the process comprising an iterative layering technique in which each layer is formed by freezing, or lyophilisation followed by re-hydration, prior to addition of a following layer. Suitably, the scaffold is collagen based, and each layer is formed from a suspension of collagen in a solvent, typically a weak acid solvent, suitably a homogenous suspension of collagen, which is initially in the form of a slurry, wherein the layer is formed (i.e. solidified) by freezing or lyophilisation. When a layer is lyophilised, the layer is typically re-hydrated using the same solvent as used in the collagen suspension, ideally a weakly acidic solvent.

In one preferred embodiment of the invention, at least two of the layers in the scaffold are formed by lyophilisation. In a preferred embodiment of the invention, all layers in the scaffold are formed by lyophilisation.

In one embodiment, the scaffold comprises two layers. In this case, steps B and C are omitted. Preferably, the scaffold has three layers, in which case step B is carried out once.

Thus, the process of the invention is an iterative process in which a first layer is formed by freezing or freeze-drying, then a subsequent layer is poured onto the first layer and the composite is frozen or freeze-dried, etc. A process in which layers are formed by freezing or freeze-drying and, after separate formation, the formed layers are adhered together by, for example gluing or suturing, is typically excluded. Where the process involves forming the layers by freezing, the final layer will be formed by freeze-drying. Where the process involves forming each layer by freeze-drying, the formed layer or layers are re-hydrated prior to pouring the next layer.

The term "homogenous suspension" should be understood to mean a suspension of collagen in a solvent (for example a weak acid) in which the collagen is homogenously distributed throughout the solvent. Techniques for providing a homogenous suspension of collagen are described below, and will be known to those skilled in the art. Ideally, the homogenous suspensions of collagen are provided in a slurry form. The suspension(s) comprise collagen, and optionally one or more additional suitable components selected from one, two or more of: a mineral phase component such as a calcium phosphate (i.e. a hydroxyapatite); a polymer, preferably a biological polymer, for example poly(lactic-co-glycolic acid) (PLGA) or alginate or a glycosaminoglycan (GAG), such as chondroitin sulphate or hyaluronic acid, or a combination of GAGs; and a biologic. The term "biologic" should be understood to mean a biologically-active molecule—examples of such molecules include nucleic acids, for example genes, DNA, RNA, low molecular weight nucleic acids, proteins, polypeptides, and peptides, hormones, growth factors, cytokines, metabolites and cells. The homogenous suspension of collagen comprises collagen homogenously distributed throughout the suspension. Typically, the collagen (and other components such as hydroxyapatite when included) is suspended in an acid solution. The molarity of the acid solution employed for making each layer may vary. Thus, in one embodiment, the molarity of the acid solution used for making the bottom layer may be 0.5 M, whereas the molarity of the solution employed in making the intermediate and top layers may 0.05 MIncases where the process involves re-hydrating a formed layer or layers, the layer(s) are re-hydrated in an acidic solution, generally a similar or identical acidic solution to that used in forming the layer.

In one embodiment, the scaffold (or each layer in the scaffold) has a porosity of at least 90%, 91%, 92%, 93%, 94%, 95%, 96%, 97% or 98%. Ideally, the scaffold has a porosity of at least 98%, ideally at least 98.5%. A method of determining % porosity is described below.

In one embodiment, the scaffold (or each layer in the scaffold) has an average pore diameter of at least 80, 85, 90, 95, 96, 97, 98, 99 or 100 microns. A method of determining average pore diameter is described below.

Typically, each layer in the scaffold is compositionally distinct. In this specification, the term "compositionally distinct" should be taken to mean that the layers differ in terms of their composition and/or morphology. In a preferred embodiment, the layers differ in terms of a parameter selected from the group consisting of: hydroxyapatite content; type of collagen; amount of collagen; type of GAG; and quantity of GAG. In one embodiment, each layer comprises one or more constituents selected from the group consisting of: Type I Collagen; a non-Type I Collagen (for example Type II Collagen); and a mineral phase (for example a hydroxyapatite). Ideally, in an embodiment in which the scaffold comprises three layers, the first layer comprises collagen and hydroxyapatite, the second layer comprises collagen and hydroxyapatite in which the collagen content is different from the first layer, and the third layer comprises collagen and little or no hydroxyapatite, and optionally a polymer and/or a biologic.

In one embodiment of the invention, the method is a method of producing a three-layer collagen scaffold that typically mimics both the morphology and composition of healthy anatomical osteochondral tissue, and in which a first outer layer comprises collagen, typically Type I collagen, and hydroxyapatite. This layer mimics the subchondral bone. Suitably, the inner layer comprises a type I collagen, non-Type I Collagen (ideally Type II collagen), hydroxyapatite and, optionally, one or more GAGs. This layer mimics the intermediate articular calcified cartilage. Typically, the second outer layer comprises a composite of Type I collagen, non-Type I collagen (ideally Type II collagen) and optionally one or more GAGs and/or a biologic. This layer mimics the overlying cartilaginous layer.

Where the scaffold is a three-layer scaffold, the method typically comprises the steps of:
preparing a first homogenous suspension of collagen and lyophilising the suspension to provide a first layer;
rehydrating the formed first layer;
preparing a second homogenous suspension of collagen and pouring the second homogenous suspension onto the re-hydrated first layer to form a two-layered composite, and lyophilising the two-layer composite;
re-hydrating the two-layer composite; and
preparing a third homogenous suspension of collagen and pouring the third homogenous suspension onto the two-layer composite to form a three-layer composite, and lyophilising the three-layer composite to form the three-layer collagen scaffold.

It will be clear that the process of the invention may be employed to produce multi-layer collagen scaffolds having two, three, four or more layers. Additionally, it will be clear that the process is an iterative process for forming a polyphasic layered scaffold in which layers are sequentially added to the composite by a process of freezing or lyophilising, and in which after pouring of a new layer, the composite layered structure is frozen or lyophilised.

Ideally, the multi-layer collagen composite scaffold is cross-linked. Typically, the composite scaffold is cross-linked by one or more of the means selected from the group comprising: dehydrothermal (DHT) cross-linking; and chemical cross-linking Suitable chemical cross-linking agents and methods will be well known to those skilled in the art and include 1-Ethyl-3-[3-dimethylaminopropyl]carbodiimide hydrochloride (EDAC) or Glutaraldehyde. Ideally, the scaffold is cross-linked using DHT and EDAC cross-linking Cross-linking can be carried out at any stage of the fabrication process. In a preferred embodiment, scaffold pore symmetry can be controlled by varying the degree of cross-linking within each respective layer using cross linking methods familiar to one skilled in the art. Similarly, in another embodiment, scaffold permeability or flow conductivity can be varied by varying the mechanical properties of the scaffold using either cross linking or other stiffness improvement methodologies known to one skilled in the art.

Typically, the first homogenous suspension comprises collagen, ideally Type I collagen, and a mineral phase, ideally hydroxyapatite (referred to herein as "bottom" or "bone" layer). Ideally, the second homogenous suspension comprises collagen, typically two types of collagen such as Type I and a non-Type I collagen (typically Type II collagen), and a mineral phase, ideally hydroxyapatite I (referred to herein as "intermediate" layer). Suitably, the third homogenous suspension comprises collagen, typically two types of collagen such as Type I and a different collagen such as Type II collagen, and optionally a polymer for example a GAG, such as chondroitin sulphate or hyaluronic acid or a combination of GAGs (referred to herein as "top" or "cartilage" layer). Typically, the pore size of the top layer is greater than that of the intermediate layer. Suitably, the pore size of the intermediate layer is greater than that of the bottom layer. The ratio of Type I collagen to Type II collagen in the top (cartilage) layer can vary from 1:0 to 0:1. Ideally, it varies from 1:4 to 4:1 (w/w).

In a preferred embodiment, the pore size and/or pore size distribution gradient are varied within each layer independently. This can be achieved for example, by varying the slurry thickness used for each layer. Additionally, the individual layer thickness can be varied in each of the layers of the multilayer scaffold between 1 mm and 15 mm using different volumes of slurry during the freezing or lyophilisation process. The shape of the scaffold produced can also be varied by using contoured trays which are tailored to the required anatomical curvature.

Thus, in a particularly preferred embodiment of the invention, the process comprises the steps of:
  preparing a first homogenous suspension of Type I collagen and HA in the form of a slurry and freezing or lyophilising the slurry to provide a first layer;
  when the first layer is formed by freeze-drying, rehydrating the formed first layer;
  preparing a second homogenous suspension of Type I collagen, a non-Type I collagen (i.e. Type II collagen), HA and optionally GAG in the form of a slurry and pouring the slurry onto the first layer to form a two-layer composite, and freezing or lyophilising the two-layer composite;
  when the second layer is formed by freeze-drying, rehydrating the second layer;
  preparing a third homogenous suspension of Type I collagen and a non-Type I collagen (i.e. Type II collagen) and optionally a polymer (for example one or more GAG's) and/or a biologic and pouring the third homogenous suspension onto the two-layer composite to form a three-layer composite, and lyophilising the three-layer composite to form the three-layer collagen scaffold; and
  optionally, cross-linking one or more of the layers of the scaffold.

Ideally, all layers of the scaffold are cross-linked in a single cross-linking step. However, each layer may be cross-linked in separate steps, for example by cross-linking a layer or layers following a freezing or lyophilisation step.

The process of the invention typically involves lyophilising the layers, either after each iterative step, and/or as part of the final step. This is a process in which the slurry is frozen, typically to a final freezing temperature of from −10° C. to −70° C. and then sublimated under pressure. In one embodiment, the desired final freezing temperature is between −10° C. and −70° C. Suitably, the desired final freezing temperature is between −30° C. and −50° C. Typically, the desired final freezing temperature is between −35° C. and −45° C., ideally about −40° C.

In one embodiment of the invention, freezing or freeze-drying is carried out at a constant cooling rate. This means that the rate of cooling does not vary by more than +/−10% of the target cooling rate, i.e. if the desired rate of cooling is 1.0° C./min, and the actual rate of cooling varied between 0.9° C./min and 1.1° C./min, this would nonetheless still be considered to be a constant cooling rate. Typically, the constant cooling rate is between 0.1° C./min to 10° C./min. Preferably, freeze-drying is carried out at a constant cooling rate of between 0.5° C./min to 1.5° C./min. More preferably, freezing or freeze-drying is carried out at a constant cooling rate of between 0.8° C./min to 1.1° C./min. Typically, freezing or freeze-drying is carried at a constant cooling rate of about 0.9° C./min. The temperature of the freeze-drying chamber at a start of the freeze-drying process (i.e. when the slurry is placed in the chamber) is usually greater than 0° C., preferably at about ambient temperature.

The sublimation step is generally carried out after the final freezing temperature is reached. This step involves heating the freeze-drying chamber to a sublimation temperature (generally about 0° C.), preferably at a constant heating rate. The process typically includes a final sublimation step where an ice phase in the formed scaffold is sublimated under vacuum for a suitable period of time.

In another embodiment of the invention, the freeze-drying process comprises an annealing step. Typically, this step involves increasing the temperature in the freeze-drying chamber after the final freezing temperature has been reached, and typically holding the increased temperature for a period of time before initiating the drying stage. For example, if the final freezing temperature is −20° C., the annealing step may be carried out by ramping up the temperature to −10° C., and holding at that temperature for a time sufficient to allow existing ice crystals grow, before finally drying the scaffold. The annealing time may be varied according to the pore characteristics desired; however, annealing times of between 15 minutes and 120 hours are preferred.

Generally, the HA employed in the present invention is in powder form. Suitably, the HA powder is selected from the group comprising: sintered HA powder; and unsintered HA powder. Examples of suitable sintered, and unsintered, HA powders suitable for the present invention will be known to the person skilled in the art, and are provided below. It will be appreciated that the HA is employed as a mineral phase in the layers where it is employed. In this regard, it will be apparent to the skilled person that the process and products of the invention may be embodied by replacing HA with an alternative mineral phase such as, for example, brushite, α-TCP or β-TCP. Other suitable mineral phase materials will be well known to the skilled person.

Typically, the HA powder has a particle size of between 10 nm and 100 μm.

Suitably, the collagen employed in the present invention comprises collagen fibres. Preferably, the collagen fibres comprise microfibrillar collagen, preferably microfibrillar bovine tendon collagen for type I collagen and porcine cartilage for type II collagen.

The homogenous suspension(s) of collagen comprises collagen suspended in an acidic solution. Typically, the acidic solution has a molarity of at least 0.01 M, Suitably, the molarity of the acidic solution is at least 0.06 M, 0.07 M, 0.08 M, 0.09 M, 0.1 M, 0.2 M, 0.3 M, 0.4 M, 0.5 M or 1 M. Ideally, the molarity of the acidic solution is between 0.4 M and 0.6 M. Ideally the acid is an organic acid, preferably acetic acid, although other organic acids may be employed.

The lyophilised layer(s) is rehydrated in an acidic solution having a molarity of preferably at least 0.015 M, preferably at least 0.02 M, and typically in a range of 0.02 M to 0.03 M, suitably about 0.023 M to 0.027 M, and ideally about 0.025 M Ideally the acid is acetic acid, although other weak organic acids may be employed.

In an embodiment of the invention in which the homogenous suspension comprises collagen and hydroxyapatite (CHA) slurry, the ratio of HA to collagen in the suspension is typically greater than 1:10 (w/w), and the molarity of the acidic solution is greater than 0.01 M. Typically, the ratio of HA to collagen in the suspension is at least 2:10 (w/w), 3:10 (w/w), 4:10 (w/w), 5:10 (w/w). In one preferred embodiment of the invention the ratio of HA to collagen is from 1:10 (w/w) to 100:10 (w/w), suitably from 1:10 (w/w) to 50:10 (w/w), suitably from 5:10 (w/w) to 30:10 (w/w).

In one preferred embodiment of the invention, the ratio of HA to collagen in the first homogenous suspension is at least 5:10 (w/w), and wherein the molarity of the acidic solution is at least 0.1 M. Typically, the molarity of the acidic solution is at least 0.50 M.

In a preferred embodiment of the invention, the ratio of HA to collagen in the first homogenous suspension is at least 1:2 (w/w), 1:1 (w/w), 2:1 (w/w), 3:1 (w/w), 4:1, or 5:1 (w/w). In one embodiment of the invention, the ratio of HA to collagen in the first homogenous suspension is greater than 5:1 (w/w). Generally, when such levels of HA are employed in the suspension, the molarity of the acidic solution will be at least 0.5 M.

In a preferred embodiment, the amount of collagen in the suspension can vary from 0.5 g/L up to 50 g/L of acid solution (1/10 and 10 times standard collagen concentration respectively). Suitably, the amount of collagen in the suspension is between 1.0 g/L and 10.0 g/L, preferably between 3.0 g/L and 8.0 g/L, and more preferably between 4.0 g/L and 6.0 g/L.

Typically, the acidic solution comprises an acetic acid solution. However, other organic acids may be employed to form the acidic solution.

Suitably, the homogenous suspensions of collagen are formed in conditions suitable for minimising gelatinisation of the collagen. One method of ensuring minimal gelatinisation of collagen during the production of the homogenous suspension is to maintain the suspension at a sufficiently low temperature, generally between 1° and 5° C., suitably about 4° C.

More recent advances in cartilage tissue engineering involve the use of scaffolds as growth factor or gene carrier systems. There are a number of essential growth factors providing regulatory effects on chondrocytes or stem cells involved in chondrocyte maturation and cartilage formation. These include the TGF-β superfamily, IFG, FGF, BMP, PDGF and EGF (Lee S H, Shin H; 2007). Miljkovic et al. (Miljkovic et al.; 2008) report on the successful delivery of BMP-4 for the treatment of cartilage defects. Thus, in one embodiment of the invention, the process includes an additional step of incorporating a biologic into the multi-layer collagen-composite scaffold. This could be achieved by, for example, soaking the prepared scaffold in a solution containing the growth factor (or cells) of interest, through cross-linking or using transcription. Suitably, the biological material (biologic) is selected from the groups of: cells; and biological growth factors. Typically, the biological growth factors are selected from the group consisting of one or more of the TGF-β superfamily, (IFG, FGF, BMP, PDGF, EGF) or cannabinoids. These growth factors can also be included during the production process as opposed to post-fabrication soaking of the scaffolds. Typically, the cells are selected from the group consisting of chondrocytes, osteoblasts or mesenchymal stem cells, although other cells may be employed. The invention also relates to a cell-seeded tissue engineering construct comprising a multilayer collagen scaffold according to the invention having cells incorporated into the scaffold, ideally into the pores of the scaffold. Cell-seeded tissue engineering constructs of the invention may be made by seeding a scaffold of the invention with cells, and then culturing the cells in-vitro, prior to use (implantation) of the construct. Accordingly, the invention also relates to a method of producing a cell seeded tissue engineering construct of the type comprising a multilayer collagen scaffold according to the invention, wherein the cells are disposed within the pores of the scaffold, the method comprising the steps of seeding cells from a host onto the scaffold, and culturing the cells on the scaffold prior to implantation into a defect.

Additionally, these scaffolds are ideally suited for use as delivery mechanisms for gene therapy delivery, either through viral or non-viral delivery vectors. The idea of a gene delivery vector contained within a biodegradable scaffold, although not new, is a recent development in the field of regenerative medicine and the system has been coined as a 'gene activated matrix' (GAM). Gene therapy can be a valuable tool to avoid the limitations of local delivery of growth factors, including short half-life, large dose requirement, high cost, need for repeated applications, and poor distribution.

The invention also relates to a multi-layer collagen scaffold obtainable by the process of the invention.

The invention also relates to the use of the multi-layer collagen scaffold obtainable by the process of the invention in repairing osteochondral defects, tendons and ligaments, vascular tissue, tracheal tissue, or skin.

The invention also relates to a multi-layer collagen scaffold comprising a plurality of freeze-dried layers in which a first layer comprises collagen, typically Type I collagen, and HA, a second layer comprises one or more types of collagen (typically Type I collagen and a non-Type I collagen such as Type II collagen), HA and optionally one or more types of GAG, and a third layer comprises one or more types of collagen (typically two types of collagen, i.e. Type I and a non-Type I collagen such as Type II collagen) and optionally one or more types of GAG and optionally a biologic. Ideally, the layers in the scaffold are adhered together. In a preferred embodiment, the layers are freeze-dried together. However, other methods for adhering the layers together will be apparent to the skilled person including, for example, suturing and adhesive. Preferably, the scaffold comprises a continuous pore architecture extending across the layers of the scaffold.

The invention also relates to a multi-layer collagen scaffold comprising a plurality of freeze-dried layers in which a first layer consists essentially of collagen and HA, a second layer consists essentially of a collagen, HA and a GAG, and a third layer consisting essentially of collagen and GAG, wherein a ratio of HA in the first layer to HA in the second layer is at least 1:1 (w/w). Typically, the ratio of HA in the first layer to HA in the second layer is at least 3:1 (w/w), preferably at least 4:1 (w/w), and ideally at least 5:1 (w/w). Suitably, the collagen component in the first layer comprises (or consists essentially of) a single type of collagen, typically Type II collagen. Generally, the collagen component of the second and third layers comprises (or consists essentially of) two types of collagen, suitably Type II and a non-Type I collagen.

The individual layer thickness can be varied in each of the layers of the multilayer scaffold between 1 mm and 15 mm using different volumes of slurry during the freezing or lyophilisation process. In a preferred embodiment, the pore size and pore size distribution gradient can be varied within each layer independently by varying the volume of slurry used to produce each layer. The shape of the scaffold produced can also be varied by using contoured trays which are tailored to the required anatomical curvature.

Thus, the invention also relates to a multi-layer collagen-composite scaffold suitable for use in tissue and bone defect repair applications or tissue engineering applications, especially osteochondral defect repair, and comprising a layered structure comprising at least three porous scaffold layers that differ in at least a parameter selected from collagen content, collagen type, and hydroxyapatite content, wherein the scaffold has a continuous, and optionally variable, pore architecture extending across the scaffold (i.e. extending across the layers). The term "continuous pore architecture" means that the porous architecture extends across three layers without being interrupted by seams formed at the interface between layers. Such a continuous (also referred to herein as "seamless") pore architecture can be clearly seen in FIG. 9 below, which shows a three-layer scaffold of the invention in which the pore structure of one layer is integrated into the pore structure of an adjacent layer without being interrupted by seams or areas of lamination. This can be contrasted with the pore structure of scaffold shown in FIG. 8 of Tampieri et al, which is clearly discontinuous and includes seams located at the interface between the 70/30 and 40/60 layers. The term "variable pore architecture" means that the pore architecture may also be variable across the layers (for example, the pore size may vary). In one embodiment, the porous structure of each layer is different, for example the formed scaffold may have a pore size gradient extending across the layers due to each layer having different pore size characteristics.

The invention also relates to a multi-layer collagen scaffold comprising a plurality of porous freeze-dried layers in which the scaffold has a continuous pore architecture extending across the layers, and in which the pore architecture of at least two of the layers is typically different. Ideally, the scaffold comprises a pore architecture gradient extending across the layers. This means that one or more pore architecture characteristic, for example, pore size, pore size homogeneity or pore size distribution, is varied across the layers in a graded manner (for example, the pore size may increase from one layer to the next, or the pore size homogeneity may increase from one layer to the next). The pore architecture can also be varied in a manner that will result in a small pore size in the central layer and larger pore sizes in the outer layers, or vice versa.

The invention also relates to a multi-layer collagen scaffold comprising a plurality of porous freeze-dried layers in which the interface between each layer is seamless, and in which the pore architecture of at least two of the layers is typically different. Suitably, the multi-layer collagen-composite scaffold is provided in the form of a core.

The invention also relates to a seamlessly integrated multilayer scaffold formed in a process that employs an iterative layering process that allows independent control of (a) cooling rate (b) final freezing temperature, (c) freezing gradient experienced by each layer.

The invention also relates to an integrated multilayer scaffold with continuous physical integration at the interface of each adjacent layer, wherein each layer comprises a pore architecture characteristic that is different to the other layers. The pore architecture characteristic is for example selected from pore size, pore size homogeneity and pore size distribution.

A highly porous multilayer/multi-region scaffold with distinct but physically integrated regions, independently controlled pore size and pore architecture in each region of the scaffold, with a region optimised to produce maximum cartilage production, a region optimised to produce maximum bone production and an intermediate region optimised to produce calcified cartilage in between.

An integrated multilayer scaffold with distinct regions that have continuous physical integration across the layer interfaces/interfacial regions, in which each layer has at least one characteristic selected from pore size, pore homogeneity, pore size distribution, composition and mechanical properties that is different from the other layers.

A multilayer/multi-region scaffold with a continuous physical interface between adjacent layers which allows a high degree of cellular infiltration across all regions of the scaffold and which has the optimal composition, pore architecture, porosity and mechanical properties to induce the differentiation of mesenchymal stem cells (MSCs) into chondrocytes in the cartilage region of the scaffold and into osteoblasts in the bone region of the scaffold.

A multilayered, integrated scaffold replicating the anatomical composition and structure of native osteochondral tissue for use in the repair of osteochondral tissue.

The term "integrated" as used above should be understood to mean that the pore architecture of adjacent layers is continuous and not interrupted by seams or voids.

A highly porous scaffold with a functionally graded structure, with varying composition, pore size, pore homogeneity, permeability and mechanical properties, optimised for the repair of an osteochondral defect.

The invention also relates to a method of repairing a tissue defect such as an osteochondral defect in a mammal, comprising the steps of providing a multi-layer collagen scaffold of the invention, shaping the scaffold to fit into the defect, optionally soaking the scaffold, either before or after shaping, in a solution of biological material, and inserting the scaffold into the defect. Optionally, the biological material can be incorporated into the scaffolds during the fabrication process. Typically, the scaffold has a base layer comprising collagen and HA, and wherein the scaffold is inserted into the defect such that the base layer abuts the deepest part of the defect. In one embodiment, the defect is also shaped to ensure a good fit between the defect and the scaffold. Examples of other tissue defects that may be repaired using the scaffolds of the invention include mandibular/maxillofacial defects, cardiovascular defects, tracheal reconstruction, cartilage defect repair within any articulating joint within the skeletal system (e.g. hip, knee, shoulder, ankle, hand, foot, neck, spine), any soft tissue defect within the body, rheumatoid arthritis, osteoarthritis, any form of arthritis resulting in cartilage damage, repair of collateral damage at articulating joints due to trauma (e.g. Anterior Cruciate Ligament, torn rotator cuff, dislocated/broken ankle, meniscal repair), ankle joint repair and soft tissue reconstruction (maxillofacial, tissue augmentation).

BRIEF DESCRIPTION OF THE FIGURES

FIG. 3: XRD patterns for the pure HA powder in blue and the bottom layer CHA scaffold in black, with the characteristic peaks for HA in red. (Bottom layer CHA scaffold=200 wt % HA). This shows that HA is successfully incorporated into the scaffold and that its phase purity is unaffected by the process.

FIG. 4: Comparison of the mechanical properties of a standard collagen scaffold, the bottom or bone layer (Layer 3—containing type I collagen and 200 wt % HA), the intermediate layer (Layer 2—containing equal amounts of type I collagen, type II collagen and HA) and the top or cartilage layer (Layer 1—containing equal amounts of type I and type II collagen), and a 3-layer scaffold following DHT treatment at 105° C. for 24 hours.

FIG. 5: Permeability of the individual scaffold layers compared to that of a pure collagen scaffold. (Bottom layer CHA=200 wt % HA, Intermediate layer=type I collagen in 0.05 M acetic acid: type II collagen in 0.05 M acetic acid: 200 wt % HA in 0.5 M acetic acid (1:1:1), Top layer=type I collagen in 0.05 M acetic acid: type II collagen in 0.05 M acetic acid (1:1).

FIG. 6: Representative micrographs of the pore structure of each of the component layers of the 3-layer scaffold produced in isolation showing the homogeneous pore architecture. (Bottom layer CHA=200 wt % HA, Intermediate layer=type I collagen in 0.05 M acetic acid: type II collagen in 0.05 M acetic acid: 200 wt % HA in 0.5 M acetic acid (1:1:1), Top layer=type I collagen in 0.05 M acetic acid: type II collagen in 0.05 M acetic acid (1:1)).

FIG. 10: Cell numbers for 3-layer scaffolds compared to collagen scaffolds at 7 and 14 days showing an increase in cell number of approximately 50% from day 7 to day 14 for both the collagen and the 3-layer scaffolds. (Bottom layer CHA=200 wt % HA, Intermediate layer=type I collagen in 0.05 M acetic acid: type II collagen in 0.05 M acetic acid: 200 wt % HA in 0.5 M acetic acid (1:1:1), Top layer=type I collagen in 0.05 M acetic acid: type II collagen in 0.05 M acetic acid (1:1). This example was produced using the 'iterative layering technique' and freeze-drying using a freezing temperature of −40° C.).

FIG. 11: Scaffold contraction of the 3-layer scaffold compared to a standard collagen scaffold at 7 and 14 days post seeding with MC3T3-E1 mouse pre-osteoblast cells. The 3-layer scaffold was found to contract to a lesser extent than the standard collagen scaffold. (Bottom layer CHA=200 wt % HA, Intermediate layer=type I collagen in 0.05 M acetic acid: type II collagen in 0.05 M acetic acid: 200 wt % HA in 0.5 M acetic acid (1:1:1), Top layer=type I collagen in 0.05 M acetic acid: type II collagen in 0.05 M acetic acid (1:1). This example was produced using the 'iterative layering technique' and freeze-drying using a freezing temperature of −40° C.).

FIG. 12: Histologically prepared, haematoxylin and eosin (H&E) stained transverse sections of the 3-layered scaffold following 14 days in vitro culture with MC3T3-E1 mouse pre-osteoblast cells. (Bottom layer CHA=200 wt % HA, Intermediate layer=type I collagen in 0.05 M acetic acid: type II collagen in 0.05 M acetic acid: 200 wt % HA in 0.5 M acetic acid (1:1:1), Top layer=type I collagen in 0.05 M acetic acid: type II collagen in 0.05 M acetic acid (1:1). This example was produced using the 'iterative layering technique' and freeze-drying using a freezing temperature of −40° C.).

DETAILED DESCRIPTION OF THE INVENTION

Materials and Methods

EXAMPLE 1

Figure 1:
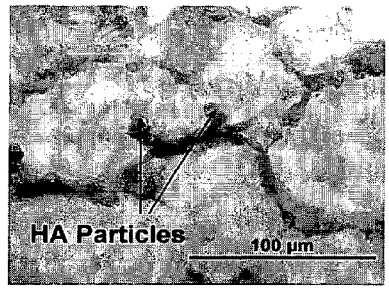
FIG. 1: Toluidine blue stained 10 μm transverse section of the bottom CHA layer of a 2-layer scaffold, showing the presence of hydroxyapatite (HA) particles within the scaffold struts. This confirms that HA remains within the scaffold during the 'iterative layering process'. (Bottom layer CHA scaffold=200 wt % HA)

Embodiment 1 relates to the production of a two layer scaffold using the 'iterative freeze-drying' technique. The invention consists of a base bone layer composed of type I collagen and preferably 200 wt % hydroxyapatite, but this can range from 0 wt % HA up to 500 wt % HA. The top cartilage layer is composed of type I and type II collagen. The ratio of type I collagen to type II collagen can be from 0:1 to 1:0.

The preferred 200 wt % collagen/HA (CHA) slurry for the bone layer of the scaffold is prepared as follows: 240 ml of preferably 0.5 M acetic acid (this can range from 0.05 M to 10 M) was prepared by adding 6.9 ml glacial acetic acid to 233.1 ml of distilled deionised water. 1.2 g of microfibrillar bovine tendon collagen (Collagen Matrix Inc., N.J., USA) was placed into a beaker and 100 ml of 0.5 M acetic acid solution was added. The beaker was refrigerated at 4° C. overnight to allow the collagen to swell and thus blend more easily. A WK1250 water cooling system (Lauda, Westbury, N.Y., USA) was used to cool a glass reaction vessel to 4° C. The collagen and acetic acid solution were added to the reaction vessel. 100 ml of the 0.5 M acetic acid solution was added to the beaker to remove any remaining collagen and then poured into the reaction vessel. The components were blended using an IKA Ultra Turrax T18 overhead blender (IKA Works Inc., Wilington, N.C.) at 15,000 rpm for 90 minutes. The slurry components were maintained at 4° C. during blending to prevent denaturation of the collagen as a result of the heat generated during the process.

2.4 g hydroxyapatite (HA) powder (Captal 'R' Reactor Powder, Plasma Biotal, UK) was added to 40 ml of the 0.5 M acetic acetic solution. The HA acetic acid suspension was mixed in a syringe-type delivery device creating a homogenous suspension of HA particles within the acetic acid solution. 10 ml of the HA suspension was added to the collagen slurry during blending by placing the tip of the HA delivery device tube into the vortex centre created by the blender. This ensured rapid dispersion of the HA suspension through the collagen slurry. 10 ml of the HA suspension were added to the slurry every hour (4 additions of 10 ml of HA suspension in total).

The slurry was blended for a further 60 minutes following addition of the final 10 ml of HA giving a total blend time of 330 minutes (5½ hours). The interval between the addition of the aliquots of the HA suspension can be varied from 30 to 240 minutes. The number of additions can also be varied, preferably HA is added in at least 2 aliquots.

CHA slurries containing other quantities HA can be produced by varying the quantity of HA added, for example, for a 100 wt % CHA slurry, 1.2 g of HA powder would be added to 40 ml of 0.5 M acetic acid. Examples of such slurries are described in International Patent Application (Publication) No. WO2008/096334 (Royal College of Surgeons in Ireland).

Following blending, the slurry was degassed in a conical flask connected to a vacuum pump for 30 minutes to remove unwanted air bubbles within the slurry. 15.6 ml of the slurry was then placed in a 60 mm×60 mm square 304 grade stainless steel tray. The slurry was then freeze-dried in a Virtis (VirTis Co., Gardiner, N.Y., USA) freeze-drier. The freeze-drying cycle used can be varied in order to produce scaffolds with different pore structures. This is achieved by varying the freezing temperature used from −10° C. to −70° C. The −40° C. freeze-drying cycle consisted of the following steps: The tray was placed on a shelf in the freeze drier at 20° C. The cycle involved cooling the shelf to −40° C. at a preferred constant rate of 0.9° C./min, based on the findings of a previous study (O'Brien FJ; 2004). The cooling rate selected can range from 0.1° C./min to 10° C./min. The shelf temperature was then held constant for 60 minutes to complete the freezing process. The shelf temperature was then ramped up to 0° C. over 160 minutes. The ice phase was then sublimated under a vacuum of 200 mTorr at 0° C. for at least 17 hours to produce the porous CHA scaffold.

A type I Collagen (Col1) Slurry was Produced as Follows:

The preferred Col1 slurry contains 5 g/l of type I collagen suspended in 0.05 M acetic acid. The quantity of Col1 can be varied between 5 g/l and 50 g/l. The acetic acid concentration used can range between 0.01 M and 10 M. 240 ml of 0.05 M acetic acid was prepared by adding 0.69 ml glacial acetic acid to 239.31 ml of distilled deionised water. 160 ml of 0.05 M acetic acid was added to 0.8 g of Col1 and left to swell overnight in the refrigerator at 4° C. A WK1250 water cooling system (Lauda, Westbury, N.Y., USA) was used to cool a glass reaction vessel to 4° C.

The collagen and acetic acid solution was added to the reaction vessel and the components were blended for 90 minutes. Following blending, the slurry was degassed in a conical flask connected to a vacuum pump for 30 minutes to remove unwanted air bubbles within the slurry. The slurry was placed in a bottle and stored in a refrigerator at 4° C. The acetic acid concentration used to produce the Col1 slurry can be varied from 0.01 M and 10 M.

Iterative Layering Process

The bone layer CHA scaffold was rehydrated in an acetic acid solution in order to prevent collapse of the scaffold following addition of the second layer slurry and also to prevent excessive infiltration of the second layer slurry into the base scaffold. The concentration of the acetic acid solution can be varied from 0.001 M acetic acid to 5 M, with 0.025 M acetic acid solution being the preferred concentration. 800 ml of 0.025 M acetic acid was prepared by adding 1.1 ml glacial acetic acid to 798.9 ml of distilled deionised water. Rehydration involved filling the 60mm×60mm freeze-dying tray with acetic acid and placing the scaffold into it. This was then placed under vacuum until the scaffold was fully rehydrated and air bubbles had been removed from the scaffold. Excess acetic acid was removed using a pipette. 15.6 ml of the top layer collagen slurry was carefully pipetted on top. The two layer construct was then returned to the freeze-dryer and freeze-dried using the freeze-drying process described above.

EXAMPLE 2

Embodiment 2 relates to a three layer scaffold, the base layer of the scaffold has similar structural and compositional properties to the subchondral bone layer and consists of the primary constituents of bone; type I collagen (the organic phase) and hydroxyapatite (the mineral phase). The intermediate layer has a similar composition to calcified cartilage and consists of type II collagen which is present in cartilage and also type I collagen and hydroxyapatite (present in bone). The top layer, modelled on the superficial to the deep zones of articular cartilage, comprises type I and type II collagen.

Bone Layer:

The bone layer consisted of a CHA scaffold, with the amount of HA present varying between 0 wt % and 500 wt %. The CHA slurry was fabricated and freeze-dried as described in embodiment 1 above.

Intermediate Layer:

The intermediate layer consisted of type I collagen (Col1) (Collagen Matrix Inc., N.J., USA), type II collagen (Col2) (Porcine type II collagen, Biom'up, Lyon, France) and hydroxyapatite (HA) (Captal 'R' Reactor Powder, Plasma Biotal, UK).

A type I (Col1) slurry was produced as described in embodiment 1. The type II collagen (Col2) slurry can contain from 5 g/l to 50 g/l type II collagen. The 5 g/l Col2 slurry is produced by placing 0.2 g of Col2 into a glass beaker and then adding 40 ml of acetic acid solution. The acetic acid concentration used can be varied from 0.01 M to 0.5 M. The solution was refrigerated at 4° C. overnight to allow the collagen to swell. The solution was placed on ice and blended using a homogeniser for 30 minutes to produce a homogenous slurry. The slurries containing the greater quantities of Col2 are produced by increasing the amount of Col2 added, for example a 1% Col2 slurry contains 0.4 g of Col2 in 40m1 of 0.05 M acetic acid.

The intermediate layer slurry was produced by combining the CHA slurry, Col1 slurry and Col2, produced as described in embodiment 1 and 2, slurry into a glass beaker. The 3 slurries were mixed by blending using a homogeniser for 30 minutes until a homogenous solution was produced. The homogenous slurry was then degassed to remove air bubbles by placing the beaker in a vacuum chamber connected to a vacuum pump. The amount of each component slurry in the intermediate layer can be varied between 0% and 100%.

Prior to addition of the intermediate layer slurry to the bone layer scaffold, the bone layer scaffold was rehydrated. This is necessary in order to prevent scaffold collapse. The preferred rehydration medium was a 0.025 M acetic acid solution. 800 ml of 0.025 M acetic acid was prepared by adding 1.1 ml glacial acetic acid to 798.9 ml of distilled deionised water. A 60 mm×60 mm square 304 grade stainless steel tray was used for producing the layered scaffolds. A CHA bone layer scaffold was produced and rehydrated as described in embodiment 1. 15.6 ml of the intermediate layer slurry was pipetted on top of the rehydrated CHA bone layer. The quantity added to each one can be varied to give an intermediated layer thickness of between 1 mm and 15 mm. The 2-layer construct was then freeze-dried as described in embodiment 1.

Cartilage Layer:

The cartilage layer slurry was produced by placing the Col1 slurry and Col2 slurry, produced as described above, into a beaker, placing the beaker on ice and then blending until a homogenous solution was produced. The homogenous slurry was then degassed to remove air bubbles by placing the beaker in a vacuum chamber connected to a vacuum pump. The ratio of the Col1 slurry to the Col2 slurry (Col1 :Col2) can vary from 0:1 to 1:0 Prior to addition of the cartilage layer, the 2-layer scaffold was rehydrated in acetic acid as previously described. The cartilage layer slurry was pipetted on top of the rehydrated 2-layer scaffold, the quantity used ranging from 3 ml to 60 ml, to give a scaffold ranging from 1 mm to 15 mm, depending on the thickness required. The entire structure was freeze-dried again to produce a 3-layer scaffold.

Following freeze-drying the 3-layer porous structure was crosslinked using a dehydrothermal cross-linking process (DHT). This involved placing the structure in a vacuum oven (Fisher IsoTemp 201, Fisher Scientific, Boston, Mass.) to crosslink the collagen and thus provide an increase in the mechanical strength of the structure. Cross-linking can carried out at a temperature of from 105° C. to 180° C. under a vacuum of 50 mTorr for 24 hours.

EXAMPLE 3

In another example, a 3-layered scaffold is produced where the base layer is crosslinked via a chemical cross-linking method described earlier (EDAC) prior to addition of the $2^{nd}$ layer in order to improve mechanical stiffness of the scaffold and maintain a equiaxed pore structure when additional layers are added to the scaffold. The degree of cross-linking used can be controlled based on the structural requirements.

EXAMPLE 4

Embodiment 4 relates to an alternative method for the production of layered tissue engineering scaffolds. The process involves producing a collagen based slurry as above, and pipetting the 67.5 ml of the slurry into a 127 mm×127 mm square 304 grade stainless steel tray. This tray is then placed in the freeze-dryer and the slurry is frozen to a temperature of between −10° C. and −70° C. at a preferred constant rate of 0.9° C./min. This freezing rate can be varied between 0.1° C./min and 10° C./min. The shelf temperature was then held constant for 60 minutes to complete the freezing process. The frozen scaffold was then removed from the freeze-dryer and 67.5 ml of a second slurry layer was applied on top. The 2-layer structure was then freeze-dried. The cycle involves cooling the shelf to a temperature of between −10° C. and −70° C. at a constant rate of 0.9° C./min. The shelf temperature was then held constant for 60 minutes to complete the freezing process. The shelf temperature was then ramped up to 0° C. over 160 minutes. The ice phase was then sublimated under a vacuum of 200 mTorr at 0° C. for at least 17 hours to produce the 2-layer porous scaffold.

EXAMPLE 5

Embodiment 5 relates to a 3-layered scaffold and the method of fabrication. The process involves the production of a collagen based slurry as above, and pipetting 67.5 ml of the slurry into stainless steel tray as described above. The tray is placed into the freeze-dryer and the slurry is frozen to a temperature of between −10° C. and −70° C. at a suitable constant freezing rate, preferable 0.9° C./min. The shelf temperature was held constant for at least 60 minutes to complete the freezing process. A second slurry layer was applied to this frozen slurry and the >60 minute freezing step was repeated. The frozen 2-layer material was then removed from the freeze-dryer and a $3^{rd}$ collagen-based slurry was again pipetted on top. This was then returned to the freeze-drying and freeze-dried using a freeze-drying cycle where the shelf was cooled to a temperature of between −10° C. and −70° C. at a constant rate of 0.9° C./min. The shelf temperature was then held constant for 60 minutes to complete the freezing process. The shelf temperature was then ramped up to 0° C. over 160 minutes. The ice phase was then sublimated under a vacuum of 200 mTorr at 0° C. for at least 17 hours to produce a 3-layer scaffold.

EXAMPLE 6

A further embodiment relating to the scaffold disclosed here relates to the use of the scaffold as a growth factor delivery carrier system. Growth factors that could be incorporated into the scaffold include the TGF-β superfamily, IFG, FGF, BMP, PDGF, EGF and cannabinoids. These growth factors could be included into the scaffold in a number of ways, including by soaking the prepared scaffold in a solution containing the growth factor of interest, through cross-linking, using transcription, or through other methods.

Characterisation of Scaffolds

The properties of the individual scaffold layers and layered scaffolds produced in this study were compared to a control scaffold made of type I collagen, fabricated using the standard protocol as detailed above. Briefly, a slurry was produced using 5 g/l type I collagen in 0.05 M acetic acid solution and lyophilised at a constant cooling rate to a final freezing temperature of −40° C.

Mechanical Stiffness

In order to ensure survival following implantation the mechanical properties of the implant must be sufficient to withstand the forces experienced during load bearing. The mechanical properties of the scaffold have also been shown to affect cellular response (Engler et al.; 2006). The differentiation lineage for MSCs was found by Engler et al. to vary depending on substrate elasticity, with a neuronal phenotype resulting on soft substrates and osteoblasts resulting on high stiffness substrates. The mechanical properties would thus have particular importance in applications where defect healing occurs due to the infiltration of MSCs, for example, if the scaffold was to be used in combination with the microfracture technique. Mechanical testing was carried out on 9.7 mm diameter samples using the Zwick Z050 Mechanical Testing Machine (Zwick/Roell, Germany). Prior to testing samples were pre-hydrated with phosphate buffered saline (PBS). The scaffolds were loaded at a strain rate of 10% per minute and the modulus was defined as the slope of a linear fit to the stress-strain curve over the 2-5% strain range.

The mechanical properties of each individual layer of the 3-layer scaffold produced in isolation and of the 3-layer scaffold were determined and compared to a standard collagen scaffold. The results are shown in FIG. 4. The bottom layer was found to have the highest compressive modulus of approximately 0.95 kPa, significantly higher than the other two groups ($p<0.05$). This is due to the presence of the HA mineral phase. The compressive moduli of the intermediate layer and the top layer were found to be between approximately 0.3 kPa and 0.4 kPa, with no significant difference being found between the two groups. The compressive modulus of the 3-layer scaffold was found to be similar to that of the collagen scaffold, with no statistically significant difference ($p>0.05$) being found between the two groups.

Distribution of Hydroxyapatite (HA)

Figure 3:
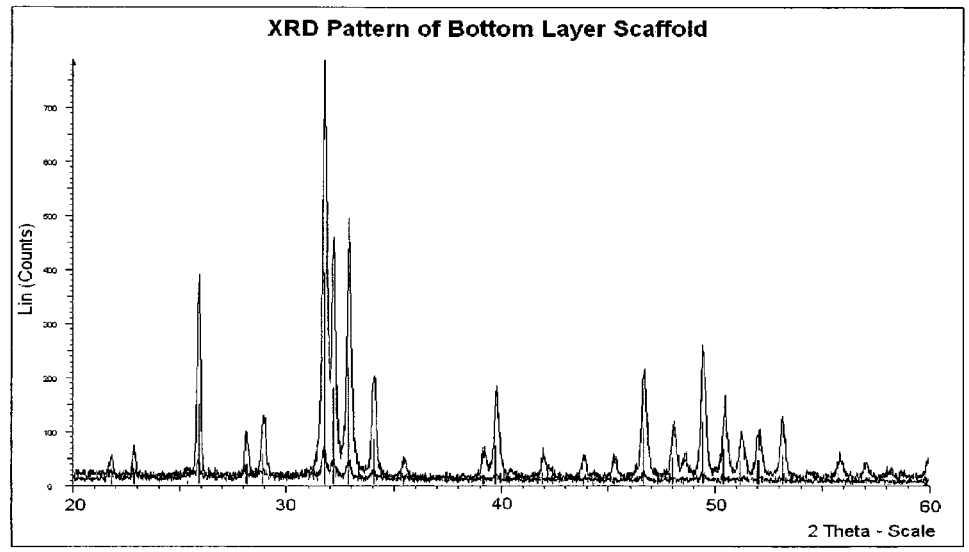
FIG. 3 shows a micrograph of histological sections of the 2 layer 200 wt % CHA (base layer)/Col1 (top layer) scaffold imaged using light microscopy. The micrographs indicate that the base 200 wt % layers retains its pore structure during the 'iterative freeze-drying' process. The top layer also displays equiaxed pore morphology.

The distribution of hydroxyapatite (HA) within a 2-layer scaffold was investigated by embedding the scaffold in a polymer, carrying out histological preparation and then staining with Toluidine blue stain. Microscopic analysis enabled HA distribution to be examined. The presence of HA particles within the collagen struts is evident, as shown in FIG. 1. X-ray diffraction (XRD) was used to analyse the effect of the fabrication process on the chemical composition of the bottom layer CHA scaffold. The XRD pattern for the bottom layer scaffold was compared to that of the pure HA powder and to the standard XRD pattern for HA (JCPDS 72-1243). The results, shown in FIG. 3, confirm the presence of HA in the bottom layer CHA scaffold. No other calcium phosphate phases were identified, thus confirming that degradation of the HA component has not occurred.

Scaffold Permeability

The permeability of a porous material is the ease with which a fluid can flow through it. High permeability is essential for tissue engineered scaffold materials in order to allow cellular migration into their centre. The permeability of the individual layers of the 3-layer scaffold is compared in FIG. 5. Scaffold permeability can be seen to relate to substrate stiffness, with the scaffolds which were found to have a higher compressive modulus displaying the greatest permeability. The permeability of our 3-layer scaffold can be controlled by altering the mechanical properties of the individual scaffold layers, in order to produce an optimal scaffold.

Porosity and Pore Structure

A high level of porosity is a vital requirement for scaffolds used for tissue regeneration in order to allow the infiltration of cells, diffusion of nutrients and removal of waste. If the porosity is insufficient avascular necrosis will occur at the centre of the implanted material, leading to failure of the construct. One of the main advantages of the present invention is the high degree of porosity within all regions of the scaffold. The porosity of each of the component layers of the 3-layer scaffold was determined using the density method as per F2450-04: Standard Guide for Assessing Microstructure of Polymeric Scaffolds for Use in Tissue Engineered Medical Products, using the following formulae $$V_p = V_T - \frac{m_s}{\rho_s}$$

$$\% \text{ Porosity} = V_p / V_T \times 100$$

Where $V_p$ is the volume of the pores in the scaffold, $V_T$ is the total volume of the scaffold, determined by measuring the sample dimensions, $m_s$ is the mass of the scaffold, and $\rho_s$ is the density of the material.

Figure 7:
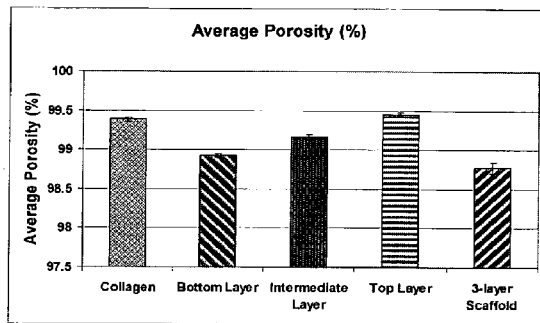
FIG. 7: Porosity of a standard collagen scaffold, each of the component layers of the 3-layer scaffold produced in isolation, and a 3-layer scaffold, showing the high porosity of all scaffold variants. (Bottom layer CHA=200 wt % HA, Intermediate layer=type I collagen in 0.05 M acetic acid: type II collagen in 0.05 M acetic acid: 200 wt % HA in 0.5 M acetic acid (1:1:1), Top layer=type I collagen in 0.05 M acetic acid: type II collagen in 0.05 M acetic acid (1:1))

The average porosity of each layer is shown in FIG. 7. The top layer was found to have the highest porosity and the bottom layer the lowest. The difference between groups was found to be statistically significant ($p<0.05$). A reduction in porosity was seen due to the addition of HA particles but this is negligible in real terms (99.5-98.8%). A high level of porosity is necessary in order to ensure the infiltration of cells into the centre of the scaffold and also the supply of nutrients and removal of waste from these cells. If porosity is insufficient, areas of necrosis will result within the scaffold.

The pore size and pore structure of scaffold materials is also important. A homogenous interconnecting pore structure with optimal pore size is necessary in order to successfully generate repair tissue. If pores are too small cell migration is limited, whereas if pores are too large there is a decrease in surface area, limiting cell adhesion (O'Brien F J, 2005; Murphy C M, 2009). One of the advantages of the freeze-drying process used to produce the scaffolds detailed in this invention is the ability to precisely control pore size and pore homogeneity. The pore structure of the individual scaffold layers and of 2-layer scaffolds was analysed by embedding the scaffold in JB4 glycomethacrylate (Polysciences, Germany), in both longitudinal and transverse plane, preparing the scaffolds histologically and staining them with toluidine blue prior to microscopic analysis. Representative micrographs demonstrating the pore homogeneity of the individual scaffold layers are shown in FIG. 6. These micrographs demonstrate that the addition of type II collagen and hydroxyapatite to the various layers does not effect pore homogeneity.

Figure 8:
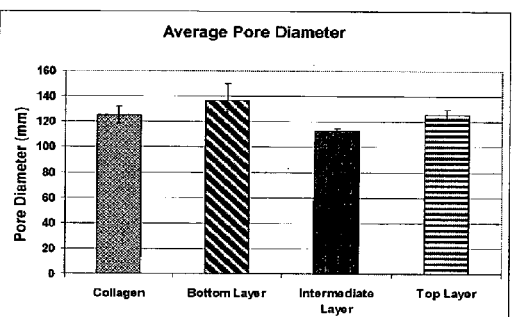
FIG. 8: Comparison of the pore diameters of each of the component layers of the 3-layer scaffold produced in isolation. The average pore diameters were found to vary from 112 μm (intermediate layer scaffold) 136 μm (bottom layer scaffold). (Bottom layer CHA=200 wt % HA, Intermediate layer=type I collagen in 0.05 M acetic acid: type II collagen in 0.05 M acetic acid: 200 wt % HA in 0.5 M acetic acid (1:1:1), Top layer=type I collagen in 0.05 M acetic acid: type II collagen in 0.05 M acetic acid (1:1)).

Pore size was determined using a linear intercept method. The average pore sizes of the individual scaffold layers produced in isolation using a −40° C. freeze-drying cycle, are shown in FIG. 8. The average pore diameters were found to range from 112 μm for the intermediate scaffold to 136 μm for the bottom scaffold. The pore size of each individual layer can be controlled by altering the freezing temperature used during the freeze-drying process.

Figure 2:
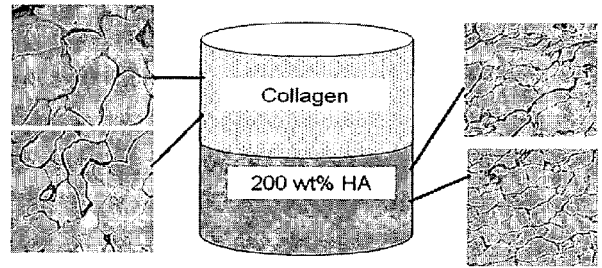
FIG. 2: Pore structure of the 2-layer 200 wt % CHA/Col1 Scaffold. The scaffold pore structure was investigated by embedding the scaffold and then sectioning it to a thickness of 10 μm using a microtome. The slices were mounted on a glass slides and the scaffold struts were stained using Toluidine blue stain.

A homogenous pore structure is also obtained when producing layered scaffolds. The microscope images of sections from both the top and bottom layers of a 2-layer scaffold shown in FIG. 2 demonstrate the capability of the 'iterative layering' method to produce a layered construct with a highly porous structure and homogenous pore size distribution throughout.

Figure 9:
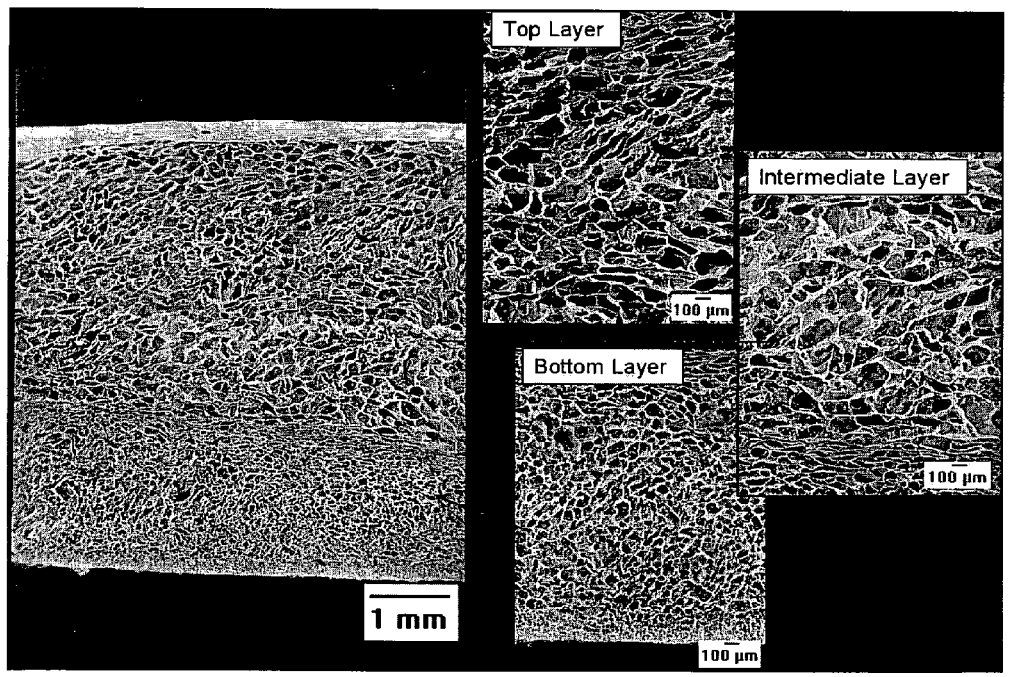
FIG. 9: SEM micrographs of the 3-layer scaffold showing the highly porous structure, high degree of pore interconnectivity and seamless integration of the component layers. (Bottom layer CHA=200 wt % HA, Intermediate layer=type I collagen in 0.05 M acetic acid: type II collagen in 0.05 M acetic acid: 200 wt % HA in 0.5 M acetic acid (1:1:1), Top layer=type I collagen in 0.05 M acetic acid: type II collagen in 0.05 M acetic acid (1:1). This example was produced using the 'iterative layering technique' and freeze-drying using a freezing temperature of −40° C.).
Figure 13:
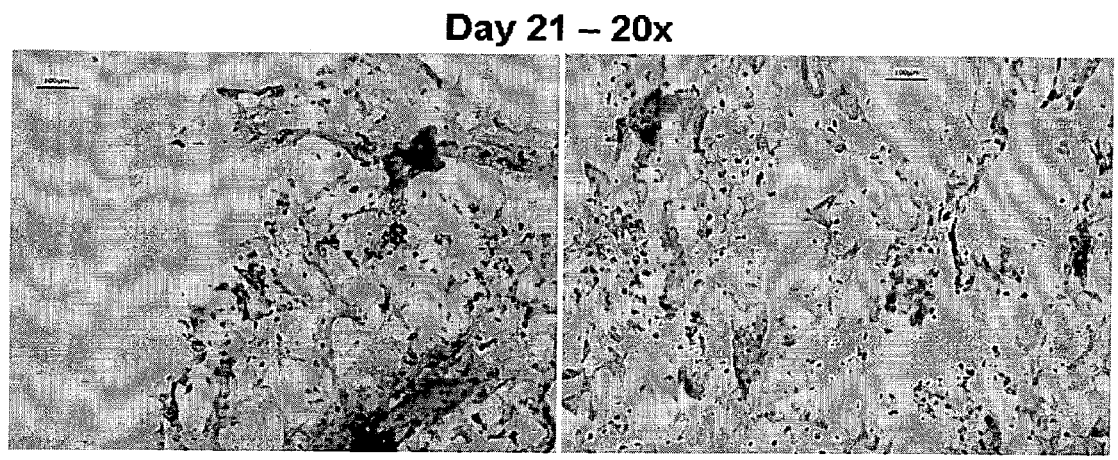
FIG. 13: Histological image of a type I collagen/hyaluronic (HyA) acid scaffold containing 10 mg/ml of HyA, following 21 days culture with rat MSCs in chondrogenic medium, stained with fast green, safranin-O and Haemotoxylin.
Figure 14:
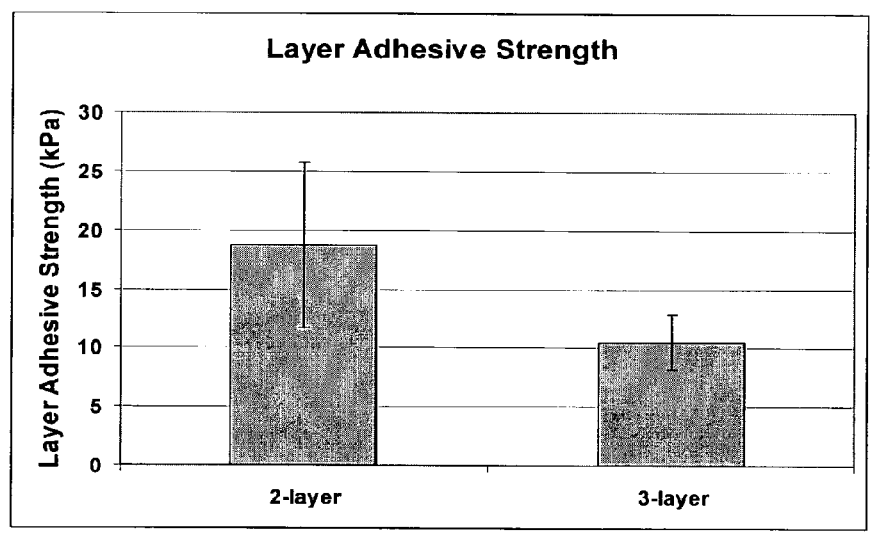
FIG. 14: Layer adhesion strength test results for the 2-layer and 3-layer scaffolds. (2-layer scaffolds=Bottom layer CHA=200 wt % HA, Top layer=type I collagen in 0.05 M acetic acid; 3-layer scaffolds=Bottom layer CHA=200 wt % HA, Intermediate layer=type I collagen in 0.05 M acetic acid: type II collagen in 0.05 M acetic acid: 200 wt % HA in 0.5 M acetic acid (1:1:1), Top layer=type I collagen in 0.05 M acetic acid: type II collagen in 0.05 M acetic acid (1:1). Both produced using the 'iterative layering technique' and freeze-drying using a freezing temperature of −40° C.).
Figure 15:
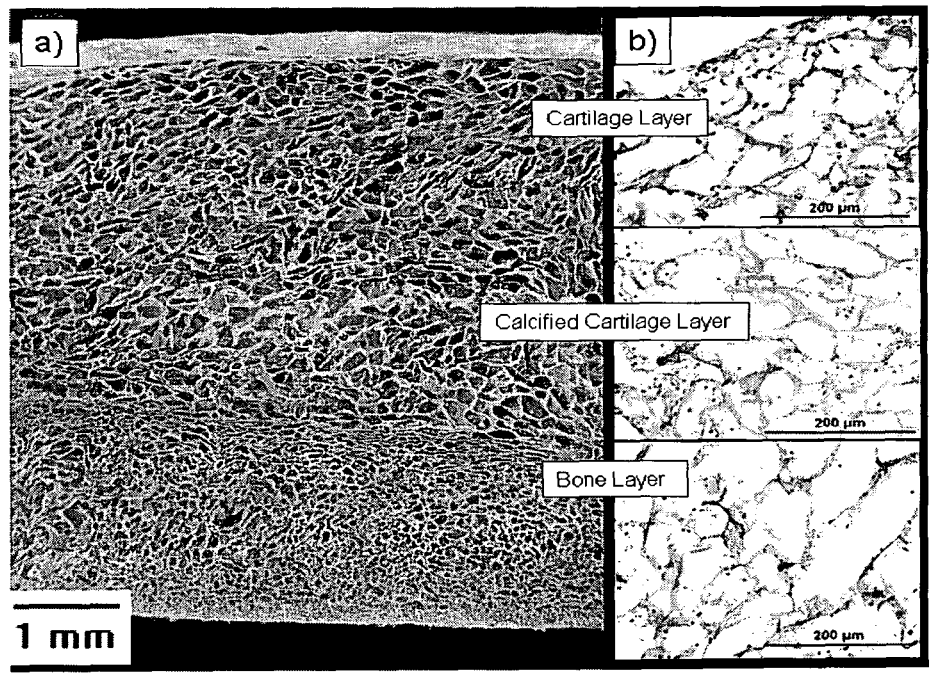
FIG. 15: 3-layered scaffold a) SEM image showing scaffold microstructure b) H&E stained sections at 14 days post seeding
Figure 16:
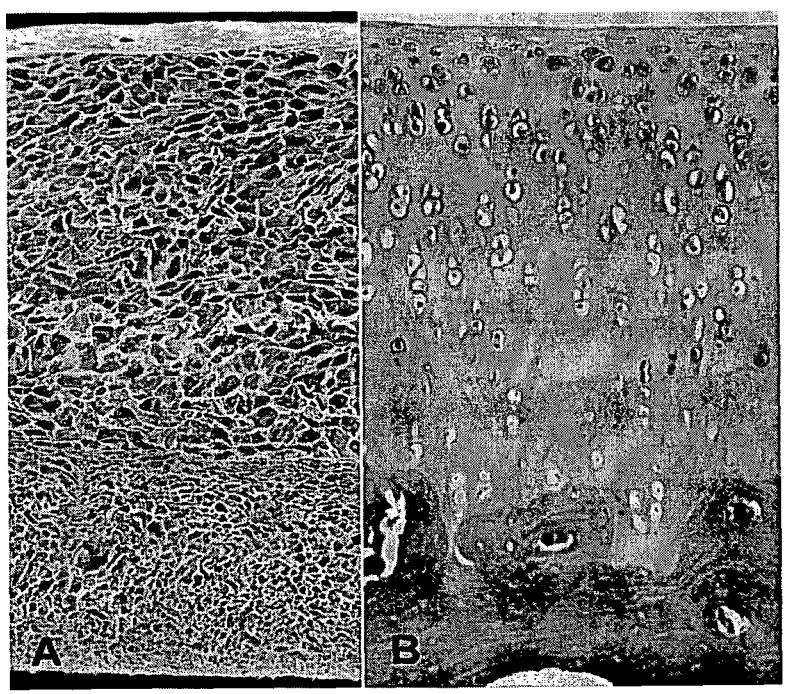
FIG. 16: A—ChondroCol1—3 layered scaffold. B—Histological images of normal cartilage superficial, intermediate and deep zones showing orientation of chondrocytes.
Figure 17:
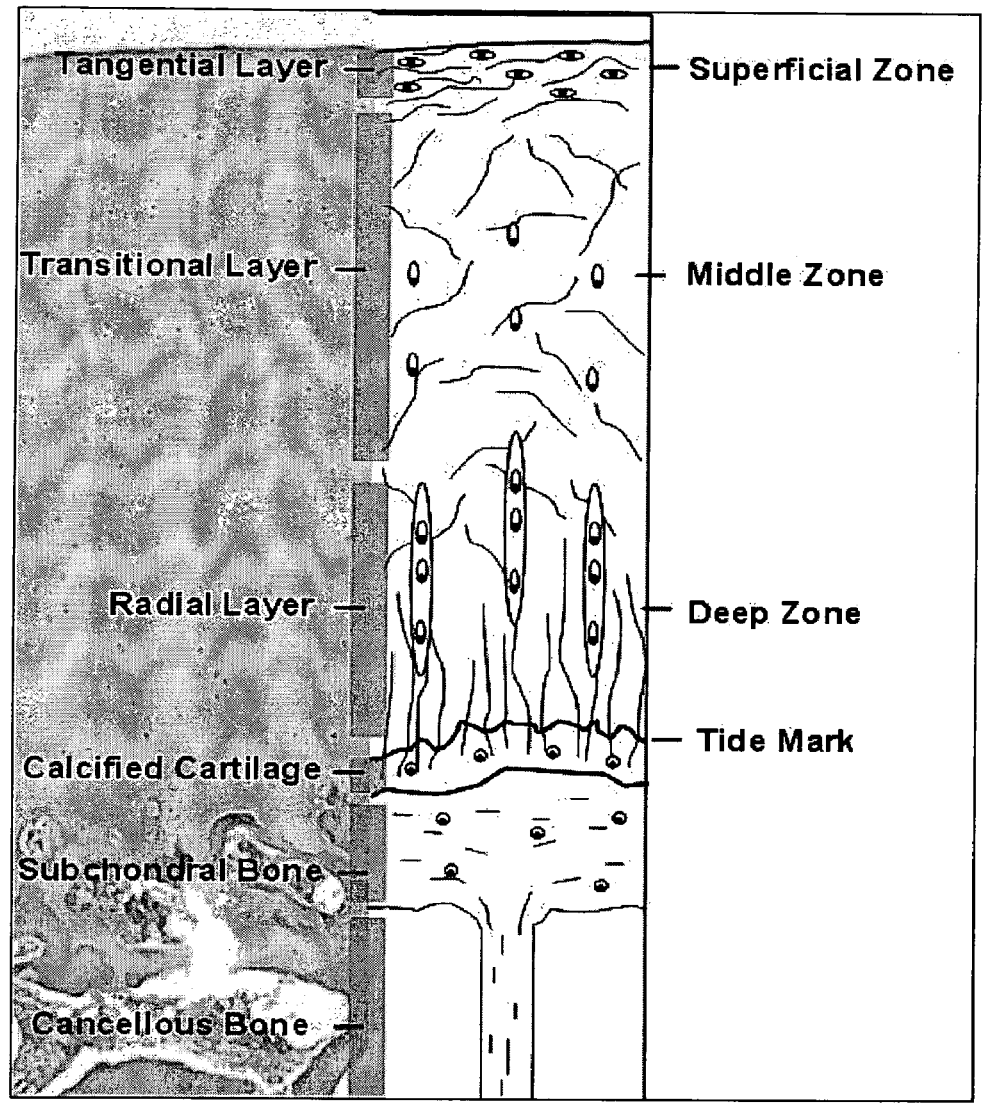
FIG. 17: Histological images of normal cartilage superficial, intermediate and deep zones showing orientation of chondrocytes.

Scanning Electron Microscopy (SEM) analysis of the 3-layered scaffold (FIG. 9) demonstrates the high degree of pore interconnectivity throughout the construct. Structural continuity at the interfaces is evident, with the individual layers being seamlessly integrated. This seamless integration of the scaffold layers is vital in order to promote the regeneration of anatomical repair tissue. This type of continuous structure cannot be achieved using other layered scaffold production methods which involve for example the suturing or gluing together of the scaffold layers.

In-vitro Bioactivity

The ability of cells to attach to, infiltrate through, and proliferate within the 3-layered scaffold described in this invention was investigated through in vitro culture. Scaffold discs, 12.7 mm (½") in diameter and 4 mm in height, were cut from pre-fabricated scaffold sheets of the 3-layered scaffold material. The scaffolds were seeded with MC3T3-E1 mouse pre-osteoblast cells at a density of $2 \times 10^6$ cells per scaffold. Scaffolds were evaluated at 7 and 14 days post seeding. FIG. 12 shows transverse sections of a 3-layer scaffold, following 14 days in culture, prepared histologically and stained using haematoxylin and eosin (H&E) staining Cells were seen to infiltrate into scaffold and adhere to the collagen struts.

Cell number was determined by DNA quantification using Hoechst DNA assay. Qiazol Lysis Reagent was used to allow dissociation of nucleoprotein complexes. Hoechst 33258 dye was then added to fluorescently label DNA and fluorescent emission was read using a fluorescence spectrophotometer. Readings were converted to cell number using a standard curve. Cells numbers for the collagen and 3-layer scaffolds at 7 and 14 days are shown in FIG. 10. There was an increase in cell number of approximately 50% from day 7 to day 14 for both the collagen and the 3-layer scaffolds, indicating that cells are readily proliferating within both scaffold types. This demonstrates that the scaffolds are highly biocompatible, providing an excellent environment for the growth and differentiation of the MC3T3 cells.

Interfacial Adhesion Strength

The interfacial adhesion strength between the layers of the multi-layer construct described here is an important property. If adhesion strength is insufficient delamination will occur at the layer interfaces. Interfacial adhesion strength of both 2-layer and 3-layer constructs was determined using a custom designed rig fitted to the Zwick Z050 Mechanical Testing Machine (Zwick/Roell, Germany). Testing involved adhering the scaffold to test stubs using a high viscosity adhesive. A tensile load was applied to samples at a strain rate of 10% per minute. The samples were tested to failure. Pre-hydration of samples in PBS was carried out prior to testing and testing was carried out in a bath of PBS to maintain hydration during the test period. Fibre pullout was observed on the fracture surface following testing indicating true integration of the scaffold layers.

The invention is not limited to the embodiment hereinbefore described which may be varied in construction and detail without departing from the spirit of the invention.

REFERENCES

Aigner T, Stove, 2003—Collagens—major component of the physiological cartilage matrix, major target of cartilage degeneration, major tool in cartilage repair, Advanced Drug delivery Reviews 55 (2003) 1569-1593

Newman A P, 1998—Newman A. P., (1998), Current Concepts, Articular Cartilage Repair, The American Journal of Sports Medicine, Vol. 26., No. 2

Beris A E 2005—Beris A. E., et al. (2005), Advances in articular cartilage repair, Injury, The International Journal of the Care of the Injured, 36S, S14-S23

Hunziker E B, 2001—Hunziker E B (2001) Growth-factor-induced healing of partial-thickness defects in adult articular cartilage, Osteoarthritis Cartilage 9: 22-32.

Sherwood J K et al, 2002—Sherwood, J. K., (2002), A three-dimensional osteochondral composite scaffold for articular cartilage repair, Biomaterials 23 4739-4751

Engler 2006—Engler A. J., Sen S., Sweeney H. L., Discher D. E. Matrix Elasticity Directs Stem Cell Lineage Specification. Cell, Volume 126, Issue 4, Pages 677-689.2006

Lee S H, Shin H: 2007—Lee, S. H., Shin, H., (2007), Matrices and scaffolds for delivery of bioactive molecules in bone and cartilage tissue engineering, Advanced drug delivery reviews,59:339-359

Miljkovic et al, 2008—Miljkovic N. et al. (2008) Chondrogenesis, bone morphogenetic protein-4 and mesenchymal stem cells, Osteoarthritis and Cartilage, Volume 16, Issue 10, Pages 1121-1130

O'Brien F J, 2005—O'Brien F. J., Harley B. A., Yannas I. V., and Gibson L. J. The effect of pore size on cell adhesion in collagen-gag scaffolds. Biomaterials, 26:433-441,2005

Murphy C M, 2009—Murphy C. M., (2010) The effect of mean pore size on cell attachment, proliferation and migration in collagen-glycosaminoglycan scaffolds for bone tissue engineering, Biomaterials, Volume 31, Issue 3, January 2010, Pages 461-466

The invention claimed is:

1. A multilayer collagen scaffold comprising a three freeze-dried layers in which a first layer comprises Type I collagen and HA, a second layer comprises Type I collagen and a Type II collagen and HA, and a third layer comprises Type I and Type II collagen and a polymer and/or biologic.

2. A three-layer collagen scaffold as claimed in claim 1 in which the polymer in the third layer comprises a GAG.

3. A multi-layer collagen scaffold comprising a plurality of freeze-dried layers in which a first layer consists essentially of collagen and HA, a second layer consists essentially of a collagen and HA, and a third layer consisting essentially of collagen, wherein a ratio of HA in the first layer to HA in the second layer is at least 1:1 (w/w), wherein the collagen component in the first layer comprises Type I collagen, and the collagen component of the second and third layers comprises Type I and II collagen.

4. A multi-layer collagen scaffold as claimed in claim 3 in which the ratio of HA in the first layer to HA in the second layer is at least 3:1 (w/w).

5. The multi-layer collagen scaffold of claim 3, wherein the scaffold has a continuous pore architecture extending across the layers.

6. A multi-layer collagen scaffold as claimed in claim 5 in which the porous scaffold layers are seamlessly integrated.

7. A multi-layer collagen scaffold comprising a plurality of porous freeze-dried layers in which the scaffold has a continuous pore architecture extending across the layers, and in which the pore architecture of at least two of the layers is typically different.

8. A multi-layer collagen scaffold as claimed in claim 5 in which the scaffold comprises a pore architecture gradient extending across the layers.

9. A multi-layer collagen scaffold comprising a plurality of porous freeze-dried layers in which the interface between each layer is seamless, and in which the pore architecture of at least two of the layers is typically different.

10. A multilayer collagen scaffold with continuous physical integration at the interface of each adjacent layer, wherein each layer comprises a pore architecture characteristic that is different to the other layers.

11. A multilayer collagen scaffold as claimed in claim 10 in which the pore architecture characteristic is selected from pore size, pore size homogeneity and pore size distribution.

12. A multilayer collagen scaffold of claim 1 that is capable of inducing the differentiation of mesenchymal stem cells (MSCs) into chondrocytes in the cartilage region of the scaffold and into osteoblasts in the bone region of the scaffold.

13. A multilayer collagen scaffold of claim 1 in which the scaffold has a porosity of at least 95%.

14. A multilayer collagen scaffold of claim 13 in which the scaffold has a porosity of at least 98%.

15. A multilayer collagen scaffold of claim 1 in which the scaffold has an average pore diameter of at least 90 microns.

* * * * *